（12) United States Patent
Howarth et al.

(10) Patent No.: US 6,965,035 B1
(45) Date of Patent: Nov. 15, 2005

(54) COMPACTED FORMS OF HALOGENATED HYDANTOINS

(76) Inventors: Jonathan N. Howarth, 3925 Scenic Dr., Apt. No. 149, Modesto, CA (US) 95255; Bruce C. Peters, 8705 Gail Dr., Baton Rouge, LA (US) 70809

(*) Notice: Subject to any disclaimer, the term of this patent is extended or adjusted under 35 U.S.C. 154(b) by 0 days.

(21) Appl. No.: 10/202,954

(22) Filed: Jul. 25, 2002

(51) Int. Cl.$^7$ .................. C07D 233/86; A01N 43/50
(52) U.S. Cl. .................. 548/320.5; 424/405; 510/192
(58) Field of Search .................. 548/320.5; 510/192; 424/405

(56) References Cited

U.S. PATENT DOCUMENTS

| | | |
|---|---|---|
| 2,130,805 A | 9/1938 | Levine |
| 2,392,505 A | 1/1946 | Rogers |
| 2,398,598 A | 4/1946 | Rogers |
| 2,779,764 A | 1/1957 | Paterson |
| 2,795,556 A | 6/1957 | Quinn |
| 2,868,787 A | 1/1959 | Paterson |
| 2,920,997 A | 1/1960 | Wolf et al. |
| 2,971,959 A | 2/1961 | Waugh et al. |
| 2,971,960 A | 2/1961 | Waugh et al. |
| 3,121,715 A | 2/1964 | Waugh et al. |
| 3,147,259 A | 9/1964 | Paterson |
| 3,345,371 A | 10/1967 | Paterson |
| 3,626,972 A | 12/1971 | Lorenzen |
| 4,078,099 A | 3/1978 | Mazzola |
| 4,092,285 A | 5/1978 | Leo et al. |
| 4,126,717 A | 11/1978 | Mazzola |
| 4,136,052 A | 1/1979 | Mazzola |
| 4,199,001 A | 4/1980 | Kratz |
| 4,242,216 A | 12/1980 | Daugherty et al. |
| 4,270,565 A | 6/1981 | King, Sr. |
| 4,293,425 A | 10/1981 | Price |
| 4,327,151 A | 4/1982 | Mazzola |
| 4,331,174 A | 5/1982 | King, Sr. |
| 4,427,692 A | 1/1984 | Girard |
| 4,465,839 A | 8/1984 | Schulte et al. |
| 4,532,330 A | 7/1985 | Cole |
| 4,534,963 A | 8/1985 | Gordon |
| 4,535,003 A | 8/1985 | Ogawa et al. |
| 4,537,697 A | 8/1985 | Girard |
| 4,560,766 A | 12/1985 | Girard et al. |
| 4,571,333 A | 2/1986 | Hsiao et al. |
| 4,597,941 A | 7/1986 | Bottom et al. |
| 4,621,096 A | 11/1986 | Cole |
| 4,651,177 A | 3/1987 | Morishita et al. |
| 4,654,424 A | 3/1987 | Girard et al. |
| 4,659,359 A | 4/1987 | Lorenz et al. |
| 4,662,387 A | 5/1987 | King, Sr. |
| 4,677,130 A | 6/1987 | Puzig |
| 4,692,335 A | 9/1987 | Iwanski |
| 4,698,165 A | 10/1987 | Theyson |
| 4,713,079 A | 12/1987 | Chun et al. |
| 4,728,453 A | 3/1988 | Choy |
| 4,745,189 A | 5/1988 | Lee et al. |
| 4,780,197 A | 10/1988 | Schuman |
| 4,803,079 A | 2/1989 | Hsiao et al. |
| 4,839,224 A | 6/1989 | Chou et al. |
| 4,867,895 A | 9/1989 | Choy |
| 4,919,841 A | 4/1990 | Kamel et al. |
| 4,925,866 A | 5/1990 | Smith |
| 5,076,315 A | 12/1991 | King |
| 5,137,563 A | 8/1992 | Valkanas |
| 5,218,983 A | 6/1993 | King |
| 5,338,461 A | 8/1994 | Jones |
| 5,339,889 A | 8/1994 | Bigham |
| 5,384,102 A | 1/1995 | Ferguson et al. |
| 5,403,813 A | 4/1995 | Lichti et al. |
| 5,422,126 A | 6/1995 | Howarth et al. |
| 5,476,116 A | 12/1995 | Price et al. |
| 5,520,711 A | 5/1996 | Helmin |
| 5,565,109 A | 10/1996 | Sweeny |
| 5,565,576 A | 10/1996 | Hall et al. |
| 5,578,559 A | 11/1996 | Dolan et al. |
| 5,591,692 A | 1/1997 | Jones et al. |

(Continued)

FOREIGN PATENT DOCUMENTS

CA          1230825         12/1987

(Continued)

OTHER PUBLICATIONS

Al-Zahrani, S.M.; "Utilization of Polyethylene and Paraffin Waxes as Controlled Delivery Systems for Different Fertilizers"; Ind. Eng. Chem. Res., 2000;vol. 39; pp. 367-371.

(Continued)

*Primary Examiner*—Kamal A. Saeed
(74) *Attorney, Agent, or Firm*—Jeremy J. Kliebert (57) ABSTRACT

This invention provides a method of producing granules. This method comprises roll compaction of a 1,3-dihalo-5,5-dimethylhydantoin/binder blend, followed by feeding the compacted product obtained from the roll compactor into a mechanical device, where the compacted product is broken into granules. The blend comprises (i) at least one powdery or finely-divided 1,3-dihalo-5,5-dialkylhydantoin in which each halogen atom is either chlorine or bromine, in which one of the alkyl groups in the 5-position is a methyl group, in which the other alkyl group in the 5-position has in the range of 1 to 4 carbon atoms, and in which the particle size is larger than about 20 microns, and (ii) a binder quantity of a micronized synthetic polyolefin-based hydrocarbon wax. The binder quantity of wax is in the range of about 0.5 to about 2 wt %, based on the total weight of the 1,3-dihalo-5,5-dialkylhydantoin and the wax. The granules are produced at an increased granulation productivity in comparison to granules of the same 1,3-dihalo-5,5-dialkylhydantoin produced without a binder.

39 Claims, 1 Drawing Sheet

U.S. PATENT DOCUMENTS

| | | | |
|---|---|---|---|
| 5,603,941 | A | 2/1997 | Farina et al. |
| 5,610,126 | A | 3/1997 | Barford et al. |
| 5,614,528 | A | 3/1997 | Jones et al. |
| 5,670,451 | A | 9/1997 | Jones et al. |
| 5,750,061 | A | 5/1998 | Farina et al. |
| 5,753,602 | A | 5/1998 | Hung et al. |
| 5,756,440 | A | 5/1998 | Watanabe et al. |
| 5,763,376 | A | 6/1998 | Ward et al. |
| 5,780,641 | A | 7/1998 | Yerushalmi et al. |
| 5,859,060 | A | 1/1999 | Platt |
| 5,942,153 | A | 8/1999 | Heydel |
| 5,958,853 | A | 9/1999 | Watanabe |
| 5,972,864 | A | 10/1999 | Counts |
| 5,981,461 | A | 11/1999 | Counts et al. |
| 5,984,994 | A | 11/1999 | Hudson |
| 6,294,510 | B1 | 9/2001 | Norman et al. |
| 6,495,698 | B1 * | 12/2002 | Howarth ................. 548/320.5 |

FOREIGN PATENT DOCUMENTS

| | | |
|---|---|---|
| CA | 2042430 A1 | 11/1991 |
| CA | 2163596 A1 | 9/1996 |
| EP | 0106563 A1 | 4/1984 |
| EP | 0177645 A1 | 4/1986 |
| EP | 0206725 A2 | 12/1986 |
| EP | 0228593 A2 | 7/1987 |
| EP | 0581826 B1 | 9/1995 |
| GB | 1054243 | 1/1967 |
| GB | 1600289 | 10/1981 |
| GB | 2273106 A | 6/1994 |
| JP | 07171576 | 7/1995 |
| JP | 07277912 | 10/1995 |
| JP | 08027119 | 1/1996 |
| JP | 08239699 | 9/1996 |
| JP | 09087684 | 3/1997 |
| JP | 09227317 | 9/1997 |
| WO | WO 8910696 A1 | 11/1989 |
| WO | WO 9630491 A1 | 10/1996 |
| WO | WO 9715652 A1 | 5/1997 |
| WO | WO 9720546 A1 | 6/1997 |
| WO | WO 9720909 A1 | 6/1997 |
| WO | WO 9743264 A1 | 11/1997 |
| WO | WO 9743392 A1 | 11/1997 |
| WO | WO 0034186 A1 | 6/2000 |
| WO | WO 01/52651 A2 | 7/2001 |
| WO | WO 01/53209 A2 | 7/2001 |

OTHER PUBLICATIONS

Chowhan et al., "Hardness Increase Induced by Partial Moisture Loss in Compressed Tablets and Its Effect on In Vitro Dissolution"; J. Pharm. Sciences, Oct. 1978, vol. 67, No. 10, ppg. 1385-1389.

Corral et al., "Substitution in the Hydantoin Ring. III. Halogenation", J. Org. Chem., 1963, vol. 28, ppg. 1100-1104.

Jolles, "General Methods of Bromination", Bromine and its Compounds, 1966, Ernest Benn, London, ppg. 365.

Kryeer et al., "An Evaluation of Tablet Binding Agents Part II. Pressure Binders", Powder Technology, 1983, vol. 34, ppg. 53-56.

March, "Advanced Organic Chem.", 1992, 4$^{th}$ Edition, ppg. 639-640.

Markish et al., "New Aspects on the Preparation of 1,3-Dibromo-5,5-Dimethylhydantoin", Ind. Eng. Chem. Res. 1995, vol. 34, ppg. 2125-2127.

Orazi et al., "Halogenacion con 3-Bromo-5,5-Dimetil-Hidantoina", Anales Assoc. Quim. Argentina, 1949, vol. 37, ppg. 192-196. (Not translated).

Orazi et al., "Halogenacion Con 1-3-Dibromo-5,5-Dimetil-Hidantoina", Anales Assoc. Quim. Argentina, 1950, vol. 38, ppg. 5-11. (Not translated).

Petterson, "N-Halogen Compounds. I. Decomposition of 1,3-Dichloro-5,5-dimethylhydantoin in Water at pH 9", J. Org. Chem., 1959, vol. 24, ppg. 1414-1419.

Author unknown, "Big Brother Brominator-Brominators", Bulky Systems Website, <http://www.bulkysystemsinc.com/brominator/html> (Visited Aug. 10, 2001). 1 page.

Author unknown, "Bio Lab Brominator", Conely Company Website, <http://www.conelyco.com/Pool-Spa/parts/biobrom.htm> (Visited Aug. 10, 2001) 2 pages.

Hayward America's #1 Pool Water Systems Product Catalog, "Automatic Chemical Feeders" Chlorinators (Slow Dissolve Tri-Chlor Only) and Brominators, Hayward Pool Products Inc. Website, <http://www.haywardnet.com/products/catalog/displayProdInfo.cfm?itemID=61>, 2 pages.

Hayward Pool Products Owner's Guide, Installation and Operating Instructions, "Hayward Chemical Feeder", Models C250CF, C500CF, C1100CF, C1800CF, C2400CF,-1998-4 pages.

Hayward America's #1 Pool Water Systems Product Catalog, "Automatic Chemical Feeders" Chlorinators (Slow Dissolve Tri-Chlor Only) and Brominators, Buyers Guide, Hayward Pool Products Inc., Website, <http://www.haywardnet.com/products/catalog/displayProdInfo.cfm?itemID=60>, 2 pgs.

Pentair Pool Products Brochure, "Rainbow High Capacity Chlorine/Bromine Feeders", "Unsurpassed Performance From The Industry's Leader in Automatic Sanitizing of Large Residential and Commercial Pools", date unknown, 1 page.

Pentair Pool Products Brochure, "Rainbow Model 300 Automatic Chlorine/Bromine Off-line Feeders", "The Efficient, Easy Way to Sanitize Your Pool or Spa", date unknown, 1 page.

Pentair Pool Products Brochure, "Rainbow Model 320 Automatic Chlorine/Bromine In-line Feeder", "Saves Time, Reduces Manual Handling of Chemicals", date unknown, 7 pages.

Sani-King Perform-Max Pool Sanitizer Instruction Guide, Models 910, 940, & 980 (Inline) and Models 930 & 960 (Off-line), date unknown, 16 pages.

Sani-King Spa Feeder Product Brochure Model 740 from King Technology Website, <http://www.kingtechnology.com/spafeeder.htm> Visited (Aug. 10, 2001), 2000, 4 pages.

Sani-King Adjust-A-Flo Product Brochure from King Technology Website <http://www.kingtechnology.com/spafeeder.htm> (Visited Aug. 10, 2001), 2000, 1 page.

Sani-King Perform-Max Sanitizers for Inground Pools Product Brochure for Model 940 & 960 from King Technology Website, <http://www.kingtechnology.com/perfermaxIG.htm>, visited Aug. 10, 2001, 2000, 1 page.

Sani-King Perform-Max Sanitizers for Above Ground Pools Product Brochure Model 910 & 930 from King Technology Website, <http://www.kingtechnology.com/perfermaxIG.htm>, visited Aug. 10, 2001, 2000, 1 page.

Discount Pool & Spa Supplies, Automatic Chlorinators and Chemical Feeders Website, <http://www.discountpoolsupplies.com/Chemfeeders/> Visited Aug. 10, 2001, 3 pages.

Wolfgang Pietsch, "Size Enlargement by Agglomerization", John Wiley & Sons, 1991; p. 422.

Author Unknown, "Dover's Flame Retardants Protects Products Without Burning up Profits", Dover Chemical Corporation product information obtained from website http://www.dover.com/chlorez.asp?menuid=2&itemid=23; 3 pages.

Author Unknown, "Hase Petroleum Wax Co.—Candle and Other Was Products", obtained from website http://www.hpwax.com/products.htm; visited May 22, 2002, 2 pages.

Author Unknown, "Michelman Wax Types", "Michelman Performance Additives Worldwide Wax Typres & Their Properties", obtained from website http://www.performanceadditives.com/waxtypes.htm; visited May 22, 2002; 2 pages.

* cited by examiner

Figure 1

COMPACTED FORMS OF HALOGENATED HYDANTOINS

REFERENCE TO RELATED APPLICATIONS

Commonly-owned copending application Ser. No. 09/487,816 filed Jan. 18, 2000, by us, relates in part to converting 1,3-dihalo-5,5-dimethylhydantoins into compacted articles using novel binders. Commonly-owned copending application Ser. No. 09/484,938 filed Jan. 18, 2000, by one of us and some of our colleagues, describes and claims methods for effecting efficacious microbiological control utilizing 1,3-dibromo-5,5-dimethylhydantoin in novel compacted or non-compacted forms. Commonly-owned copending application Ser. No. 09/484,891 filed Jan. 18, 2000, by us, relates to the compacting of 1,3-dihalo-5,5-dimethylhydantoins other than 1,3-dibromo-5,5-dimethylhydantoin without use of binders, and to the novel compacted forms so produced. Commonly-owned copending application Ser. No. 09/483,896 filed Jan. 18, 2000, by one of us, relates to the granulation and of small average particle size 1,3-dibromo-5,5-dimethylhydantoin and also to the compaction of such granulated products to form larger-sized articles.

TECHNICAL FIELD

This invention relates to novel 1,3-dihalo-5,5-dialkylhydantoin compositions which show improved processing during compaction, and after compaction, show improved dissolution characteristics.

GLOSSARY

As used herein the terms "halogen", "halogenated", and "halo" are with reference to bromine or chlorine, or both. Also, as used herein, the term "halogenated hydantoin" refers to 1,3-dihalo-5,5-dialkylhydantoins.

BACKGROUND

As is well known, a wide variety of different products in the form of powders or small particles are converted into larger end use forms such as prills, flakes, granules, pills, caplets, tablets, wafers, briquettes, pucks, and the like. In producing such products, it is common to utilize materials known as binders. Such materials, when mixed in suitable proportions with the powder or small particles to be compacted, facilitate the production of materials having desirable physical and mechanical properties. While some binders have relatively broad application to various powdery or small particle sized products, there are a number of instances where the binder can only be used for compaction of certain products and not for others. A principal reason for such limitation is chemical incompatibility as between the binder and certain powdery or small particle sized materials. A second reason for such limitation relates to the property of certain binders to modify the solubility characteristics of the powdery or finely-divided substrate material. For example, some binders are chosen not only for their ability to facilitate compaction, but to enable more rapid disintegration of the compacted form of the material, e.g., for more rapid dissolution in water.

If the solid active ingredient dissolves too quickly for optimum performance, the active ingredient is wasted. Conversely, with a binder that retards dissolution, a much more consistent dose of the active ingredient could be applied. This would be advantageous in the area of water treatment, where, if the dissolution of a solid active ingredient such as a biocide or cleaning agent could be retarded, there would be a longer time between reapplications of the biocide or cleaning agent. Waxes have been studied in the slowing and control of the delivery of ammonium phosphate fertilizers, as reported by S. M. Al-Zahrani in *Ind. Eng. Chem. Res,* 39, 367–371, 2000. Al-Zahrani observed that fertilizer formulations which were made by melt-blending the fertilizers with 10 wt % paraffin wax or 10 wt % polyethylene wax resulted in a twofold retardation of the dissolution rate as compared to the same fertilizer in the absence of wax.

One type of material that tends to be difficult to produce in compacted forms such as tablets, granules, and briquettes is halogenated hydantoins, especially N,N'-dihalogenated dialkylhydantoin products such as 1,3-dichloro-5,5-dimethylhydantoin, N,N'-bromochloro-5,5-dimethylhydantoin, and 1,3-dibromo-5,5-dimethylhydantoin. Such materials are useful as biocides for treating water such as recreational water, cooling water, process water, and wastewater.

The N,N'-dihalogenated dialkylhydantoin products are usually formed as powdery solids. For use in many applications such as water treatment, the dry powders need to be converted into larger forms such as granules, tablets, or briquettes. This in turn has presented problems associated with providing densified or compacted products with sufficient strength to withstand the physical stresses encountered in packaging, conveying, handling, shipping, storage, and use. The nature of these problems have been described, for example, in U.S. Pat. Nos. 4,532,330; 4,560,766; 4,654,424; 4,677,130; 4,745,189; and 5,565,576. The approaches described in these patents for alleviating one or more such problems involve use of other materials. Thus in U.S. Pat. Nos. 4,532,330 and 4,621,096, halogenated dimethylhydantoins are mixed with calcium chloride and water, and the mixture is compacted by compression into the desired shape. In U.S. Pat. Nos. 4,560,766 and 4,654,424, halogenated ethylhydantoins are used instead of halogenated dimethylhydantoins and are compacted as such, or are melt blended with halogenated dimethylhydantoins. U.S. Pat. No. 4,677,130 describes forming dry blends of the halogenated dimethylhydantoin with particulate alkali metal or alkaline earth metal salt followed by compression to form a compacted product such as a tablet.

Manufacturers of halogenated hydantoins have sought to overcome these limitations by blending the materials with process additives designed to improve compaction characteristics. The presence of other halogenated hydantoins has also been indicated to provide benefits. For example, published PCT Application WO 97/43264 describes the use of 1,3-bromochloro-5-methyl-5-propylhydantoin as a binder in making compacted forms of halogenated hydantoins. The presence of hydantoins having at least one ethyl group in the 5-position is indicated to provide free flowing, dust-free powders which can be compressed into shapes without resorting to binders, as detailed in U.S. Pat. Nos. 4,427,692 and 4,560,766. In U.S. Pat. No. 4,677,130 a series of inorganic salt additives ranging from sodium carbonate to sodium metasilicate was indicated to improve the crush strength of halogenated hydantoin tablets. Inert binders such as fatty acid salts and a hectorite clay were advocated in U.S. Pat. No. 5,756,440, while the use of fatty acid amide binder additives were described in U.S. Pat. No. 5,565,576 and indicated to improve the compaction properties of halogenated hydantoins. U.S. Pat. No. 5,780,641 describes a chemical composition comprising a halogenated hydantoin mixed with dry calcium hydroxide for the purpose of facilitating processing and achieving a shape-retentive form.

Unfortunately, almost all prior efforts in the compaction of halogenated hydantoins have not provided binders having satisfactory compaction characteristics along with good chemical compatibility. Some of the classical binders (e.g., polyvinylpyrrolidinone, cellulose compounds, glues, gums, sugars, and starches) which are used to compact other products would react with halogenated hydantoins, in some cases vigorously. Moreover, a number of binder systems proposed for use with halogenated hydantoins do not provide compacted products having sufficient physical and mechanical stability. Low crush strength is often another deficiency of such compacted products.

In commonly-owned copending application Ser. No. 09/487,816 a new type of binding agent for powdery or finely-divided materials, including halogenated hydantoins, has been discovered. These binders, micronized synthetic polyolefin-based hydrocarbon waxes, produce compacted compositions of great mechanical and physical strength. Furthermore, these binders are strongly hydrophobic, and consequently can be used for modifying the dissolution or release rate of the compacted material in aqueous media.

While this is very effective, it would be desirable to minimize the amount of binder used. This would allow the delivery of more halogenated hydantoin per unit compacted composition to the end user.

This invention provides a way to minimize the amount of binder used. At the same time, the granulation productivity is further improved, and surprisingly, slower dissolution rates (and longer product life) are observed with lesser amounts of binder.

SUMMARY OF THE INVENTION

It has been found that the use of micronized polyhydrocarbon waxes as binders in blends with halogenated hydantoins leads to increased productivity during the granulation process, as compared to the granulation of halogenated hydantoins in the absence of any binder. Surprisingly, after a point, the effectiveness of the polyhydrocarbon wax binder(s) does not increase as the amount of the wax in the blend increases. More unexpected still is the greater peak load tolerated by granules made from blends having lower amounts of polyhydrocarbon wax binder.

Additionally, it has been discovered that blends of micronized polyhydrocarbon waxes with halogenated hydantoins, once compacted, show significantly retarded dissolution rates for the hydantoins in water. This effect is particularly beneficial when the compacted forms are used as solid water treatment products. The useful life of the product is prolonged, and the dosing of the product into the aqueous medium to be treated is much more consistent. Quite surprisingly, these effects have been observed when the micronized polyhydrocarbon wax was present as only 1 wt % of the blend.

An embodiment of this invention is a method of producing granules. This method comprises roll compaction of a 1,3-dihalo-5,5-dimethylhydantoin/binder blend, followed by feeding the compacted product obtained from the roll compactor into a mechanical device, where the compacted product is broken into granules. The blend comprises (i) at least one powdery or finely-divided 1,3-dihalo-5,5-dialkylhydantoin in which each halogen atom is either chlorine or bromine, in which one of the alkyl groups in the 5-position is a methyl group, in which the other alkyl group in the 5-position has in the range of 1 to 4 carbon atoms, and in which the particle size is larger than about 20 microns, and (ii) a binder quantity of a micronized synthetic polyolefin-based hydrocarbon wax. The binder quantity of wax is in the range of about 0.5 to about 2 wt %, based on the total weight of said 1,3-dihalo-5,5-dialkylhydantoin and said wax. In this embodiment, the granules are produced at an increased granulation productivity in comparison to granules of the same 1,3-dihalo-5,5-dialkylhydantoin produced without a binder. The productivity is measured after said blend or binder-free hydantoin has passed through both a roll compactor and a granulator, and is defined as the percentage of granules obtained from the granulator of at least about 6 mesh, based on the amount of blend or binder-free hydantoin fed to the roll compactor. The increased granulation productivity is defined as being at least about 10% greater for the blend than the binder-free 1,3-dihalo-5,5-dialkylhydantoin.

Another embodiment of this invention is a granule. The granule comprises a pressure compacted blend comprising (i) at least one 1,3-dihalo-5,5-dialkylhydantoin in which each halogen atom is either chlorine or bromine, in which one of the alkyl groups in the 5-position is a methyl group and in which the other alkyl group in the 5-position has in the range of 1 to 4 carbon atoms, and (ii) a binder quantity of a micronized synthetic polyolefin-based hydrocarbon wax. The binder quantity of wax is in the range of about 0.5 to about 2 wt %, based on the total weight of said 1,3-dihalo-5,5-dialkylhydantoin and said wax.

Still another embodiment of this invention is a tablet. The tablet comprises a pressure compacted blend comprising (i) at least one 1,3-dihalo-5,5-dialkylhydantoin in which each halogen atom is either chlorine or bromine, in which one of the alkyl groups in the 5-position is a methyl group and in which the other alkyl group in the 5-position has in the range of 1 to 4 carbon atoms, and (ii) a binder quantity of a micronized synthetic polyolefin-based hydrocarbon wax. The binder quantity of wax is in the range of about 0.5 to about 3 wt %, based on the total weight of said 1,3-dihalo-5,5-dialkylhydantoin and said wax.

A feature of this invention is that it is now possible to formulate blends of one or more halogenated hydantoins with one or more micronized synthetic polyolefin-based hydrocarbon wax binders so that compacted products having improved processing and dissolution properties can be produced. Adjustment of the amount of binder permits adjustments in the rate of dissolution of the 1,3-dihalo-5,5-dialkylhydantoin. In short, the dissolution characteristics of the product can be tailor-made to suit the needs of the intended usage of the product. For example, it is possible to produce a compacted form with slow dissolution properties that would be desirable in a toilet bowl puck or in a swimming pool formulation.

Other embodiments, features, and advantages of this invention will become still further apparent from the ensuing description and appended claims.

FURTHER DETAILED DESCRIPTION

The exact mechanism by which the micronized waxes perform the function of producing durable pressure compacted shapes or forms from powdery, finely-divided halogenated hydantoins is not known. Without in any way being limited by theory, it may be that the micronized wax serves in whole or in part as an adhesive or bonding agent, for example by forming, when under the compaction pressure, a film between adjacent particles that bonds the particles together and thus acts like a pressure-activated cement. It is also possible that the micronized wax serves in whole or in part as a lubricant which, by reducing the coefficient of friction among adjacent particles, enables the particles to come in closer contact with each other during application of compression pressure so that large numbers of inter-particulate bonding or fusion sites are created among the adjacent particles. It is also possible that the micronized wax enables the particles to be more readily distorted under compression pressure so that the particles can more completely bond or fuse together while under such pressure. Indeed, combinations of these and/or other mechanisms may be taking place during the application of the compression pressure to a mixture of the particulate substrate and the micronized wax.

Therefore it cannot be over-emphasized that this invention is not intended to be limited, should not be interpreted as being limited, and is not to be limited in any way to any mechanism or theory of operation. Thus, for example, while the term "binder" is used herein with reference to the micronized wax, such term is not intended to limit this invention to any mechanism, theory, or mode of operation; should not be interpreted as limiting this invention to any mechanism, theory, or mode of operation; and does not limit this invention in any way to any mechanism, theory or mode of operation. Rather the term is used to indicate that the micronized wax somehow or other functions such that when the compression pressure is released, the particles have come together into a durable form or shape that not only can be released from the mold or nip of the compression rolls without physical damage, but that possess the strength and durability to withstand the physical stresses encountered in packaging, conveying, handling, shipping, storage, and use of the compacted article. Exactly how this result actually comes about in a mechanistic or theoretical sense is immaterial to the practice of this invention.

Various micronized waxes cam be used in the practice of this invention. As noted above, these micronized waxes are typically micronized polyolefin waxes, or mixtures thereof. While the average particle size of the wax can vary within reasonable limits, preferred micronized waxes typically have, prior to compaction, an average particle size of no greater than about 15 microns. Similarly, preferred micronized waxes typically have, prior to compaction, a maximum particle size of no greater than about 40 microns. In most cases, the micronized wax has, prior to compaction, a bulk density in the range of about 0.9 to about 1.4 grams per cc at 25° C. Another characteristic of preferred micronized waxes is that they at least partially melt at a temperature in the range of about 100° C. to about 150° C.

Among particularly preferred micronized polyethylene waxes are those which, prior to compaction, (a) melt at a temperature in the range of about 109° C. to about 111° C., or (b) have an average particle size in the range of about 6.0 to about 8.0 microns, or (c) a maximum particle size of about 22 microns, or (d) have a combination of any two or all three of (a), (b), and (c).

Included among particularly preferred polypropylene waxes are those materials which are characterized, prior to compaction, by having (a) a melting temperature in the range of about 140° C. to about 143° C., or (b) an average particle size in the range of about 5.0 to about 7.0 microns, or (c) a maximum particle size of about 22 microns, or a combination of any two or all three of (a), (b), and (c).

Particularly preferred micronized wax blends include micronized polyolefin wax blends which, prior to compaction, at least partially melt at a temperature in the range of about 104° C. to about 126° C. Among these blends are those which, prior to compaction, (a) partially melt at a temperature in the range of about 104° C. to about 110° C., or (b) have an average particle size in the range of about 5 to about 7 microns, or (c) have a maximum particle size of about 22 microns, or (d) have a combination of any two or all three of (a), (b), and (c). Also included among these blends are those which, prior to compaction, (a) partially melt at a temperature in the range of about 124° C. to about 126° C., or (b) have an average particle size in the range of about 9 to about 11 microns, or (c) have a maximum particle size of about 31 microns, or (d) have a combination of any two or all three of (a), (b), and (c).

Various methods can be used in forming the dry blends used in this invention. Among preferred methods are use of ribbon blenders or tumble blenders for mixing the halogenated hydantoin and the micronized wax. Equipment of this type is readily available in the marketplace from a number of reputable suppliers. As noted above, the amount of the micronized wax in the dry blends will fall within the range of about 0.5 to about 3 wt %, based on the total weight of the halogenated hydantoin and the micronized wax. For blends which will be made into tablets, the amount of the micronized wax in the dry blends will preferably fall within the range of about 2 to about 3 wt %. Blends which will be made into granules have in the range of about 0.5 to about 2 wt %, and preferably in the range of about 0.5 to about 1 wt % micronized wax, based on the total weight of the halogenated hydantoin and the micronized wax. These ranges for the granules are preferred at least in part because, surprisingly, improved properties during and after compaction are not observed as the amount of binder is increased. Lower proportions of binder deliver more halogenated hydantoin per unit product, an advantage to the end user.

In the blending and compaction of 1,3-dihalo-5,5-dialkylhydantoins, additional components can be included in order to partake of their desirable functions and characteristics. Such additional components, often termed excipients, include lubricants, disintegrants, and mold release agents. Other optional ingredients which may be used in the formulation of products include fragrances, stabilizers, adjuvants, corrosion inhibitors, dyes, surfactants, synergists, effervescents, diluents, builders, chelating agents, buffers, and the like. Such ancillary materials should of course be compatible with the halogenated hydantoin and not interfere in any material way with its performance characteristics.

As noted above, the 1,3-dihalo-5,5-dialkylhydantoins utilized in the practice of this invention are those in which each halogen atom is either chlorine or bromine, and in which one of the alkyl groups in the 5-position is a methyl group and the other alkyl group in the 5-position is an alkyl group having in the range of 1 to 4 carbon atoms. Thus the halogenated hydantoins used in this invention include, but are not limited to, 1,3-dibromo-5,5-dimethyl-hydantoin, 1,3-dichloro-5,5-dimethylhydantoin, 1,3-bromochloro-5,5-dimethylhydantoin, 1-chloro-3-bromo-5,5-dimethylhydantoin, 1,3-dibromo-5-ethyl-5-methylhydantoin, 1,3-dichloro-5-ethyl-5-methylhydantoin, 1,3-dibromo-5-n-propyl-5-methylhydantoin, 1,3-bromochloro-5-methyl-5-n-propylhydantoin, 1,3-dibromo-5-n-propyl-5-methylhydantoin, 1,3-dichloro-5-isopropyl-5-methylhydantoin, 1,3-bromochloro-5-isopropyl-5-methylhydantoin, 1,3-dibromo-5-n-butyl-5- methylhydantoin, 1,3-dichloro-5-n-butyl-5-methylhydantoin, 1,3-dibromo-5-isobutyl-5-methylhydantoin, 1,3-bromochloro-5-isobutyl-5-methylhydantoin, 1,3-dibromo-5-sec-butyl-5-methylhydantoin, 1,3-dichloro-5-sec-butyl-5-methylhydantoin, 1,3-dibromo-5-tert-butyl-5-methylhydantoin, 1,3-bromochloro-5-tert-butyl-5-methylhydantoin, and the like, and mixtures of any two or more of them. Of these halogenated hydantoins, 1,3-dibromo-5-isobutyl-5-methylhydantoin, 1,3-dibromo-5-n-propyl-5-methylhydantoin, and 1,3-dibromo-5-ethyl-5-methylhydantoin are, respectively, preferred, more preferred, and even more preferred members of this group from the cost effectiveness standpoint.

For the 1,3-dihalo-5,5-dialkylhydantoins, it is preferred that at least one of the halogen atoms is bromine; more preferably, both halogen atoms are bromine. It is highly preferred that the other alkyl group in the 5-position of the 1,3-dihalo-5,5-dialkylhydantoin is a methyl group. Thus, highly preferred halogenated hydantoins are 1,3-bromochloro-5,5-dimethylhydantoin and 1,3-dibromo-5,5-dimethylhydantoin; the most preferred 1,3-dihalo-5,5-dialkylhydantoin employed in the practice of this invention is 1,3-dibromo-5,5-dimethylhydantoin.

When a mixture of two or more of the foregoing 1,3-dihalo-5,5-dialkylhydantoins is made up or used pursuant to this invention, the individual halogenated hydantoins of the mixture can be in any proportions relative to each other. Of the mixtures of the foregoing halogenated hydantoins that can be used pursuant to this invention, it is preferred to use 1,3-dibromo-5,5-dimethylhydantoin as one of the components, with a mixture of 1,3-dibromo-5,5-dimethylhydantoin and 1,3-dibromo-5-ethyl-5-methylhydantoin being particularly preferred.

A typical granulation process of this invention comprises roll compaction of a 1,3-dihalo-5,5-dimethylhydantoin/binder blend, which may result in the formation of sheets, sticks, or other suitable breakable shapes, followed by feeding the compacted product obtained from the roll compactor into a mechanical device, such as a Chilsonator® breaker (The Fitzpatrick Company, Elmhurst, Ill.), where the compacted product is broken into granules. A breaker device is often referred to as a granulator. In the roll compactor, the rolls are usually set to produce a sheet with a thickness in the range of about 0.025 inch to about 0.125 inch. Often, the compacted product exiting the roll compactor breaks into sticks and/or other shapes rather than forming sheets. Optionally, size classification (normally done by screening) can occur between roll compaction and breakup, after breakup, or preferably, both. When size classification is performed, undersized granules are normally recycled to the roll compactor, while oversized granules are put through the breaker device.

Thus, a preferred process of this invention comprises the following steps:
a) roll compaction of the 1,3-dihalo-5,5-dimethylhydantoin/binder blend;
b) size classification of the roll compacted product;
c) breakup of oversize particles in the breaker; and
d) size classification of the product from the breaker.

If in b) and/or d) particles are also formed that are larger and/or smaller than the selected size, it is preferred to classify the particles into (1) a fraction containing the particles in the selected size range, and (2) either or both of (i) a fraction composed of the larger particles, and/or (ii) a fraction composed of the smaller particles, as the case may be. Where a fraction of (i) exists, such fraction is preferably used in c). Where a fraction of (ii) exists, such fraction is preferably recycled to a).

The formation of granules from the 1,3-dihalo-5,5-dialkylhydantoin/binder blends can utilize conventionally known processing equipment and, for the most part, known procedures. However, in conducting granulation of the blends, it is important that the compaction pressure be sufficient to induce plastic deformation and interparticulate binding of the particles. At the same time, the compaction pressure should not be so great as to produce a compacted product which delaminates. Typically, suitable compaction pressures in the practice of this invention will fall within the range of about 500 to about 3,000 psi, and preferably in the range of about 800 to about 1,500 psi.

The time period during which the pressure is applied to the 1,3-dibromo-5,5-dimethylhydantoin solids in a) is not critical. As long as suitable compaction is achieved, the time of compaction is of little or no consequence. In any situation where the optimum time has not been previously determined, a few simple preliminary tests should readily enable such pressure conditions, including pressure times, to be determined and optimized.

The roll compaction is typically conducted at ambient room temperatures. However, it is possible to either cool or warm the material being subjected to compaction. This can be accomplished either by refrigerating or directly heating the product before introducing it into the compaction apparatus, or by chilling or heating the apparatus itself such as, for example, by using rolls equipped with heating or cooling coils or other means for effecting temperature regulation. The compaction operation itself can, and in many cases does, result in generation of heat within the compacted shape. Generally speaking, the compaction operations pursuant to this invention can be performed at temperatures in the range of about 5 to about 80° C.

It will be understood and appreciated that departures from the numerical ranges given herein for pressures and temperatures are permissible in the practice of this invention, whenever such departures are deemed necessary or desirable, provided only that such departures do not materially affect in an adverse manner the processing or the properties of the product being produced.

It would be expected that the productivity during granulation would continue to increase as the amount of binder in the blend is increased. It has been found, contrary to expectation, that increasing the amount of binder beyond a certain point does not provide a greater productivity. For the purposes of this invention, increased granulation productivity is defined as being at least about 10% greater for granulation of the blend than for the binder-free 1,3-dihalo-5,5-dialkylhydantoin. The granulation productivity is measured after 1,3-dihalo-5,5-dialkylhydantoin/binder blend or binder-free halogenated hydantoin has passed through both a roll compactor and a granulator (breaker), and is the percentage of granules obtained of at least about 6 mesh, based on the amount of blend or binder-free hydantoin fed to the roll compactor. Generally, granules obtained from the roll compactor but not fed to the granulator are included those granules obtained from the granulator when determining the productivity of the granulation process.

Average particle size and particle size distribution of the powdery or finely-divided halogenated hydantoin(s) can vary widely. One limitation is that the halogenated hydantoin(s) being compacted with the micronized wax are not so large or of such character that despite the application of the compression pressure and the presence of the micronized wax, such halogenated hydantoin(s) are incapable of being compacted and bound together into a durable form or shape. Another limitation is that the smaller amounts of micronized wax preferred herein are particularly effective with halogenated hydantoin(s) having a particle size larger than about 20 microns. Increased productivity during granulation is usually not observed for halogenated hydantoins with particle sizes smaller than about 20 microns. Typically this invention can be used successfully to form durable granules from micron-sized powders up to particles as large as about 0.5 inch. However, preferably the substrate 1,3-dihalo-5,5-dialkylhydantoin(s), and especially 1,3-dibromo-5,5-dimethylhydantoin, being shaped or formed pursuant to this invention will have particles with a particle size in the range of from about 20 microns up to about 3 U.S. Standard mesh size. Typically the average particle size of such 1,3-dihalo-5,5-dialkylhydantoins will be in the range of about 50 to about 600 microns. Preferred for use with a binder of this invention is 1,3-dibromo-5,5-dimethylhydantoin particulate solids having an average particle size in the range of about 175 to about 400 microns. Nevertheless departures from these sizes are permissible whenever deemed desirable or appropriate, and thus are within the scope of this invention.

When carrying out compaction of a 1,3-dihalo-5,5-dialkylhydantoin/binder blend, it is desirable, but not essential, to apply a pressure agglomeration lubricant to the compaction surfaces of the tooling so as to reduce the coefficient of friction between the material being compacted and the tooling. When using such lubricant, it is possible to utilize any of a variety of lubricants conventionally used for this purpose. However, a feature of this invention is that it is highly advantageous to employ, as such lubricant, a micronized wax of the type described herein. Not only is the wax a highly effective lubricant, but in addition, the resultant compacted product is free from contamination by an additional component, namely a lubricant different from the micronized wax.

When converted into granules of this invention, the 1,3-dihalo-5,5-dialkylhydantoin/binder blends result in granules able to withstand greater peak loads. The granules produced directly from the 1,3-dihalo-5,5-dialkylhydantoin/micronized wax blends have excellent peak load tolerance. As noted above, it has been discovered, contrary to expectation, that the peak load tolerance of the granules decreases as the amount of wax is increased. That is, a greater peak load tolerance for granules made from 1,3-dihalo-5,5-dialkylhydantoin/micronized wax blends is obtained when a lesser amount of micronized wax is used. Peak load tolerances for granules of this invention are preferably at least about 6.0 pounds.

Granules and tablets produced from 1,3-dihalo-5,5-dialkylhydantoins are of particular utility as biocidal agents used for treating swimming pools, spas, toilet bowl cleaners, cooling towers, air washer systems, waste water, pulp and paper processing operations, oil field applications, and decorative fountains. Procedures utilizing such articles as biocides in the treatment of water are more fully described in commonly-owned co-pending application Ser. No. 09/484,938, filed Jan. 18, 2000.

The 1,3-dihalo-5,5-dialkylhydantoins are biocidal agents for use in water treatment. These compounds are, in general, sparingly soluble in water. Thus typically for water treatment applications 1,3-dichloro-5,5-dimethylhydantoin is supplied in the form of a puck for insertion into a toilet tank. These pucks apparently are formed by use of one or more binders, such as 1,3-dichloro-5-ethyl-5-methylhydantoin and/or ethylenebis(stearamide). N,N'-bromochloro-5,5-dimethylhydantoin is supplied in solid forms such as granules, tablets, or briquettes for delivery into the water being treated by means of water flow through an erosion feeder, or in the form of pucks for insertion into a toilet tank. Here again, these solid forms apparently are produced by use of one or more binders such as 1,3-dichloro-5-ethyl-5-methylhydantoin and/or ethylenebis(stearamide).

This invention provides products in which one or more of the 1,3-dihalo-5,5-dialkylhydantoin/binder blends are converted into granules. Typical operations of this type have been described above.

While there are no hard and fast rules governing differentiation with respect to size among granules, typically granules are regarded as being particles ranging in size from about 80 to about 3 U.S. standard mesh size. It will be understood and appreciated however, that these dimensions are not intended to unduly limit the scope of this invention.

When compacted with a micronized polyolefin wax binder, granules, tablets, briquettes, or other relatively small shapes formed from the 1,3-dihalo-5,5-dialkylhydantoin/binder blends have excellent physical properties for use in water-treatment systems. The shapes erode at slow, +but essentially constant rates when maintained in a constant flow of water. The retarded dissolution rates of the compacted 1,3-dihalo-5,5-dialkylhydantoin/binder blends provide a substantially continuous amount of biocide while decreasing the frequency of replenishment of the compacted product.

It has been observed that the presence of micronized polyolefin wax in the compacted forms of 1,3-dihalo-5,5-dialkylhydantoins has a profound effect on the dissolution of the 1,3-dihalo-5,5-dialkylhydantoins. For example, granules of 1,3-dibromo-5,5-dimethylhydantoin containing only 1 wt % micronized polyethylene wax dissolved twice as slowly as 1,3-dibromo-5,5-dimethylhydantoin granules which did not contain micronized polyolefin wax. Such retarded dissolution rates are unexpected, particularly with such low levels of wax. Thus, this invention provides granules made from 1,3-dihalo-5,5-dialkylhydantoin/micronized wax blends in which the 1,3-dihalo-5,5-dialkylhydantoin in the granules dissolves at least about two times slower than the same 1,3-dihalo-5,5-dialkylhydantoin in binder-free granules on a weight basis. This invention further provides tablets made from 1,3-dihalo-5,5-dialkylhydantoin/micronized wax blends in which the 1,3-dihalo-5,5-dialkylhydantoin in the tablets dissolve at least about 2.5 times slower than the same 1,3-dihalo-5,5-dialkylhydantoin in binder-free tablets on a weight basis.

One possible explanation for the observed differences in solubility rates is that the surface of the compacted form has a greater concentration of wax than would be expected from a uniform blend (perhaps due to migration of the wax to the surface during compaction). However, this notion was disproved by a scanning electron microscope (SEM) experiment on a 1,3-dibromo-5,5-dimethylhydantoin tablet containing 3 wt % micronized polyolefin wax, which showed that the surface of the tablet was not made up entirely of wax; thus, the compacted forms are not just particles of 1,3-dihalo-5,5-dialkylhydantoin in a micronized wax holder.

The following Examples are presented to illustrate the practice of, and advantages made possible by, this invention. These Examples are not intended to limit, and should not be construed as limiting, the scope of this invention to the particular operations or conditions described therein.

EXAMPLE 1

Runs A–I used DBDMH from a process which produced single crystals. Runs J and K used 1,3-dibromo-5,5-dimethylhydantoin (abbreviated DBDMH) from a process which produced crystal agglomerates. The micronized polyethylene wax (MPP-611; Micro Powders, Inc., Tarrytown, N.Y.) was blended with the DBDMH powder prior to the tests in a 2 cubic foot (0.06 cubic meter) ribbon blender.

In the compaction runs, the procedure was as follows:

1. The starting DBDMH or DBDMH/wax blend was fed through a roll compactor with floating rolls having corrugated surfaces (CS-25, Hosokawa Bepex, Minneapolis, Minn.) at a given speed and pressure and collected. The rolls were 60 mm wide; the roll gap for all runs was 0.03 inch (0.076 cm); the feed screw speed for all runs was 1 rpm, except Run H, which had a feed screw speed of 3 rpm.

2. The compactor output was separated on a screener (LS30S666, Sweco) into smaller than 6 mesh recycle fines and 6 mesh and larger, and both cuts were weighed.

3. The 6 mesh and larger material was fed to a granulator (MGI-405, Frewitt) and reduced to less than 0.25 inch (0.625 cm) in size.

4. The granulator output was separated into 6 mesh and larger (product) and smaller than 6 mesh ($2^{nd}$ recycle fines) cuts. Both cuts were weighed.

5. The recycle fines generated in steps 2 and 4 were then blended together by hand and fed to the roll compactor as in step 1, and steps 2–4 were repeated.

weight of the product 6 mesh and larger by the total weight of starting material. In the recycle granulation step, recovery of 6 mesh and larger size particles was calculated by dividing the product cut 6 mesh and larger by the total weight of recycle fines fed (the value in the total weight column at the beginning of the recycle runs). The granulation efficiency was calculated by dividing the recovery of 6 mesh and larger weight from the granulation step by the recovery weight for the granulation step (the total weight of material recovered from the granulator). The total granulation recovery was calculated by adding together the recovery of 6 mesh and larger weights from the first set and recycle set of the granulation step and dividing the resulting value by the total weight.

TABLE 1

| Run | Pressure | Pressure, recycle | Roll speed | Roll speed, recycle |
|-----|----------|-------------------|------------|---------------------|
| A | <1000 psi | 1000 psi | 4.5 rpm | 7.7 rpm |
| B | 1000 psi | 1000 psi | 3.5 rpm | 5.4 rpm |
| C | <1000 psi | <1000 psi | 4.5 rpm | 3.5 rpm |
| D | <1000 psi | <1000 psi | 6.7 rpm | 7 rpm |
| E | <1000 psi | <1000 psi | 4.5 rpm | 7 rpm |
| F | <1000 psi | <1000 psi | 3.7 rpm | 7.3 rpm |
| G | 1000 psi | 1000 psi | 4.3 rpm | 5.6 rpm |
| H | <1000 psi | <1000 psi | 4.5 rpm | 7.8 rpm |
| I | <1000 psi | <1000 psi | 4.5 rpm | 5.7 rpm |
| J | <1000 psi | <1000 psi | 4.5 rpm | 8.3 rpm |
| K | 1000 psi | 1000 psi | 4.3 rpm | 7.7 rpm |

TABLE 2

| Run | Wax | Total weight | Initial compaction — Smaller than 6 mesh | Initial compaction — 6 mesh and larger | Initial compaction — Recovery of 6 mesh and larger | Granulation step — Smaller than 6 mesh | Granulation step — 6 mesh and larger | Granulation step — Recovery of 6 mesh and larger | Granulation step — Recovery weight | Granulation step — Granulation efficiency | Total granulation recovery |
|-----|-----|--------------|------------------------------------------|----------------------------------------|----------------------------------------------------|----------------------------------------|--------------------------------------|--------------------------------------------------|------------------------------------|-------------------------------------------|----------------------------|
| A | 0.5 wt % | 16.9 kg | 6.8 kg | 10.1 kg | 59.5% | 4 kg | 6.2 kg | 36.69% | 10.2 kg | 60.78% | |
| A recycle | | 9.9 kg | 2.9 kg | 7 kg | 70.7% | 2.6 kg | 4.2 kg | 42.42% | 6.8 kg | 61.76% | 61.54% |
| B | 0.5 wt % | 29.1 kg | 15.9 kg | 13.2 kg | 45.4% | 4.8 kg | 8 kg | 27.49% | 12.8 kg | 62.50% | |
| B recycle | | 20 kg | 13 kg | 7 kg | 35% | 2.8 kg | 4.1 kg | 20.50% | 6.9 kg | 59.42% | 41.58% |
| C | 1 wt % | 18.3 kg | 6.9 kg | 11.4 kg | 62.2% | 3.5 kg | 7.5 kg | 40.98% | 11 kg | 68.18% | |
| C recycle | | 10.6 kg | 4 kg | 6.6 kg | 62.3% | 2 kg | 4.4 kg | 41.51% | 6.4 kg | 68.75% | 65.03% |
| D | 1 wt % | 19.0 kg | 8.5 kg | 10.5 kg | 55.3% | 3.6 kg | 7 kg | 36.84% | 10.6 kg | 66.04% | |
| D recycle | | 12.5 kg | 5 kg | 7.5 kg | 60% | 2.2 kg | 4.9 kg | 39.20% | 7.1 kg | 69.01% | 62.63% |
| E | 2 wt % | 14.6 kg | 5 kg | 9.6 kg | 65.7% | 2.8 kg | 6.8 kg | 46.58% | 9.6 kg | 70.83% | |
| E recycle | | 6.4 kg | 2.1 kg | 4.3 kg | 67% | 1.2 kg | 2.9 kg | 45.31% | 4.1 kg | 70.73% | 66.44% |
| F | 2 wt % | 34.2 kg | 15 kg | 19.2 kg | 56.1% | 5.7 kg | 13.3 kg | 38.89% | 19 kg | 70.00% | |
| F recycle | | 21.0 kg | 8.2 kg | 12.8 kg | 61% | 4 kg | 8.4 kg | 40.00% | 12.4 kg | 67.74% | 63.45% |
| G | none | 15.5 kg | 8 kg | 7.5 kg | 48.3% | 3.5 kg | 4 kg | 25.81% | 7.5 kg | 53.33% | |
| G recycle | | 11.0 kg | 6 kg | 5 kg | 45.5% | 2 kg | 2.6 kg | 23.64% | 4.6 kg | 56.52% | 42.58% |
| H | none | 32.0 kg | 18.9 kg | 13.1 kg | 40.9% | 5.1 kg | 7.3 kg | 22.81% | 12.4 kg | 58.87% | |
| H recycle | | 24.5 kg | 9.5 kg | 15 kg | 61% | 6.7 kg | 8.3 kg | 33.88% | 15 kg | 55.33% | 48.75% |
| I | none | 31.1 kg | 15 kg | 16.1 kg | 51.7% | 5.8 kg | 10 kg | 32.15% | 15.8 kg | 63.29% | |
| I recycle | | 19.4 kg | 9.1 kg | 10.3 kg | 53% | 4.7 kg | 5.5 kg | 28.35% | 10.2 kg | 53.92% | 49.84% |
| J | none | 10.7 kg | 4.2 kg | 6.5 kg | 60.7% | 2.8 kg | 3.5 kg | 32.71% | 6.3 kg | 55.56% | |
| J recycle | | 7.5 kg | 3 kg | 4.5 kg | 60% | 2 kg | 2.5 kg | 33.33% | 4.5 kg | 55.56% | 56.07% |
| K | none | 13.1 kg | 6.2 kg | 6.9 kg | 52.7% | 3 kg | 3.6 kg | 27.48% | 6.6 kg | 54.55% | |
| K recycle | | 10.6 kg | 5.8 kg | 4.8 kg | 45% | 2 kg | 2.5 kg | 23.58% | 4.5 kg | 55.56% | 46.56% |

The pressure and roll speeds used in steps 1 and 5 (recycle) are summarized in Table 1.

Results from all of the compaction runs are summarized in Table 2. In the initial compaction step, the recovery of 6 mesh and larger size particles was calculated by dividing the weight of the product 6 mesh and larger by the total weight of starting material. In the granulation step, recovery of 6 mesh and larger size particles was calculated by dividing the

EXAMPLE 2

To minimize size effects, a 3.5–5 mesh cut of the granulated material was used in this experiment. Peak load tests were performed on DBDMH granules without wax, with 1 wt % wax, and with 2 wt % wax. The wax in both instances was micronized polyethylene wax (MPP-611). Granules of approximately the same size were selected by visual inspection; measurements of the thickness of the granules were not made because of the very irregular shapes of the granules. Peak load tolerance tests were performed utilizing a Sintech® 1/S compression apparatus (MTS Systems Corporation, Edenprairie, Minn.) equipped with Testworks software. The apparatus included a horizontal circular-shaped load cell interfaced with a computer, a digital micrometer also interfaced with the computer, and a vertical screw-driven piston disposed above the load cell and adapted to apply a downward force perpendicular to the load cell. Each granule was placed on its edge on the load cell with the piston in contact with at least a part of the upper edge of the granule. The piston often could not contact the entire upper edge of the granule due the irregular morphology of the granule. The piston then commenced applying a progressively increasing downward diametral force to the granule. At the same time, the load cell continuously measured the downward force being applied to the granule, and the input of such measurements was transmitted to the computer. When the force being applied reached the point where the amount of force suddenly decreased to 10% of the immediately preceding force, the granule had reached the breaking point, and the application of the force was immediately terminated by the software program. From the input to the computer, a values was provided, namely the pounds of force at the breaking point of the granule, called the peak load. The results are summarized in Table 3. The peak load values reported are each an average often runs. Numbers in parentheses are the standard deviations.

TABLE 3

| Sample | Average peak load |
| --- | --- |
| DBDMH, wax-free | 11.7 (3.4) lb. |
| DBDMH/1 wt % MPP-611 wax | 9.9 (4.3) lb. |
| DBDMH/2 wt % MPP-611 wax | 7.0 (4.0) lb. |

EXAMPLE 3

To minimize size effects, a 3.5–5 mesh cut of the granulated material was used in this experiment. The material used in Runs 1–3 were from recycle compaction, and the material used in Run 4 was from first-run compaction. The surface area of the granules was determined by the well-known nitrogen adsorption BET technique. The BET technique consists of (1) removing adsorbed gases from the sample with heat and vacuum, (2) adsorbing a mono-layer of nitrogen on the surface at liquid nitrogen temperature, (3) measuring the amount of adsorbed nitrogen, and (4) calculating the total surface area of the sample from an assumed cross-sectional area of nitrogen molecules. The total surface area was divided by the sample weight to yield the specific surface area. Specific surface area is defined as the exposed surface area of 1 gram of the sample tested. A Coulter Model 3100 instrument was used. Table 4 summarizes the results.

TABLE 4

| Run | Sample | Surface Area |
| --- | --- | --- |
| 1 | DBDMH, wax-free | 5.1 m²/g |
| 2 | DBDMH/1 wt % MPP-611 wax | 5.0 m²/g |
| 3 | DBDMH/2 wt % MPP-611 wax | 1.5 m²/g |
| 4 | DBDMH/2 wt % MPP-611 wax | 1.5 m²/g |

EXAMPLES 4–6

In the following Examples, DBDMH had been blended with various levels of micronized polyethylene wax (MPP-611; Micro Powders, Inc., Tarrytown, N.Y.). Granules and tablets were prepared from the DBDMH/wax blends.

EXAMPLE 4

A swimming pool skimmer basket was divided into two halves by means of a simple plastic partition placed across the basket diameter. One half of the basket had 50 grams of pure (wax-free) DBDMH granules placed in it. In the other half of the skimmer basket was placed 50 grams of DBDMH/1 wt % MPP-611 wax granules. Both sets of granules had been screened to a size of >8 U.S. mesh, and were of comparable size. The basket, containing both sets of granules, was introduced to the skimmer of an above-ground pool. Swimming pool water was pumped past the granules in the skimmer basket by means of the pool recirculation pump. The flow rate was around 30 gallons per minute (gpm) and the water temperature was 60° F. (15.5° C.). After 6 hours, the pump was turned off and the skimmer basket containing the partially-dissolved granules was removed. The granules were removed from their respective halves of the skimmer basket and placed in crystallizing dishes to dry overnight. Each set of granules was reweighed. The weight of the undissolved portion was subtracted from the initial weight, and the amount dissolved (the difference) was expressed in terms of % dissolved (the relative dissolution rate). Table 5 lists the relative amount dissolved for both sets of granules.

EXAMPLE 5

The procedures described in Example 4 were repeated using pure (wax-free) DBDMH granules and DBDMH/2 wt % MPP-611 wax granules. The water temperature was 66° F. (19° C.). Table 5 lists the relative amount dissolved for both sets of granules.

EXAMPLE 6

The skimmer basket setup described in Example 4 was used. In one half of the basket, tablets of DBDMH/3 wt % MPP-611 wax (5×24 g; total weight, 120 g; each tablet is 1 inch in diameter) were placed an equal distance apart from each other. In the other half of the basket, tablets of pure (wax-free) 1,3-bromochloro-5,5-dimethylhydantoin (BCDMH; 5×20 g; total weight, 100 g) were similarly arranged. Both sets of tablets were one inch in diameter, so the effective surface area exposed was approximately the same for each set of tablets. The skimmer basket containing the tablets was placed into the skimmer of an above-ground swimming pool. Pool water was pumped past the tablets in the skimmer basket by means of the pool recirculation pump. The flow rate was around 30 gpm, the water temperature was 82.1° F. (27.8° C.), and water was recirculated for 16 hours.

The tablets were dried and re-weighed. The weight of the undissolved portion was subtracted from the initial weight, and the amount dissolved (the difference) was expressed in terms of % dissolved (the relative dissolution rate). The amount of product dissolved was 75.5 g for the BCDMH tablets and 13.4 g for the DBDMH/3 wt % MPP-611 wax tablets. The BCDMH tablets dissolved at a rate 5.6 times faster (based on weight dissolved) than the DBDMH/3 wt %

MPP-611 wax tablets. Based on the respective solubility of wax-free DBDMH and BCDMH powders, a relative dissolution factor of about 2 would have been expected (with the BCDMH dissolving faster). Table 5 lists the percentage dissolved for both sets of tablets.

TABLE 5

| Example | Formulation | Amount dissolved |
|---------|-------------|------------------|
| 5 | DBDMH granules (no wax) | 44% |
| 5 | DBDMH/1 wt % MPP-611 wax granules | 21% |
| 6 | DBDMH granules (no wax) | 60% |
| 6 | DBDMH/2 wt % MPP-611 wax granules | 26.6% |
| 7 | BCDMH tablets (no wax) | 75.5% |
| 7 | DBDMH/3 wt % MPP-611 wax tablets | 11.2% |

EXAMPLE 7

Figure 1:
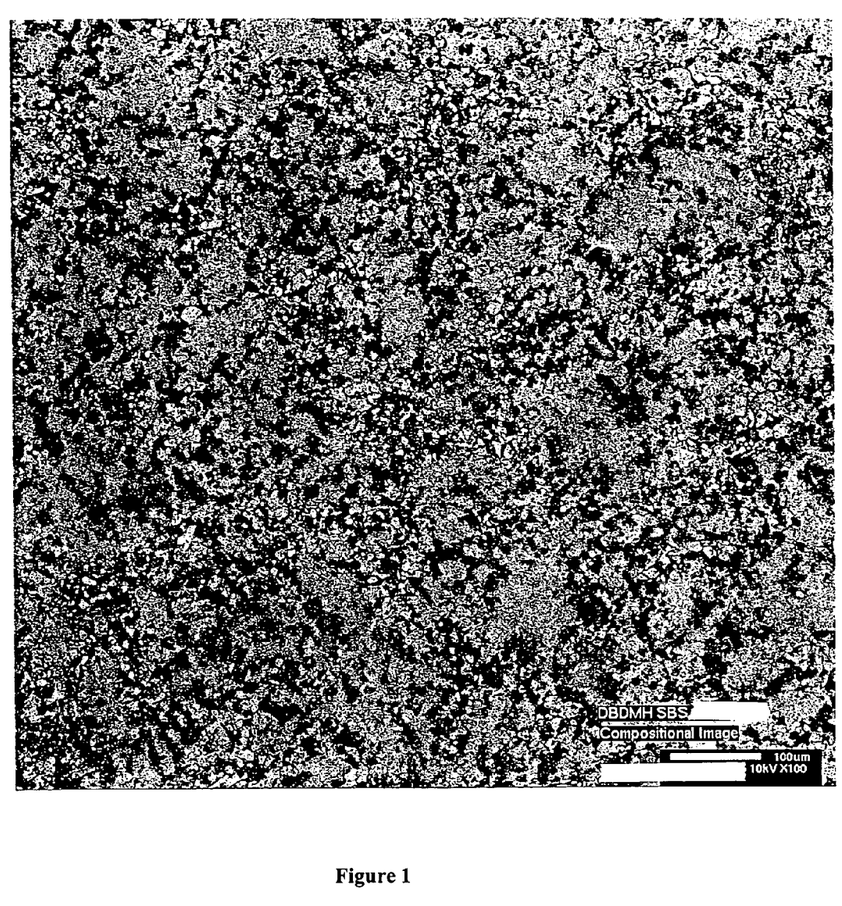
FIG. 1 is an electron micrograph from a scanning electron microscopy experiment performed on a tablet formed from a blend of 1,3-dibromo-5,5-dimethylhydantoin and 3 wt % polyethylene wax.

A tablet of DBDMH/3 wt % MPP-611 wax (24 g, 1 inch in diameter) was subjected to a scanning electron microscopy (SEM) experiment to observe the distribution of the wax and DBDMH on the surface of the tablet. The tablet was studied in the form as obtained from the tableting die; no further preparation or alteration of the sample tablet was performed. Detection was by energy dispersive x-ray diffraction spectroscopy (EDAX). The detector was tuned to the frequency of the DBDMH, which has a higher molecular weight than the wax. FIG. 1 is a micrograph showing the result; the lighter-shaded areas are DBDMH, while the darker-shaded areas are polyethylene wax. From the micrograph, it can be seen that the surface is mostly DBDMH, with the polyethylene wax distributed uniformly throughout. Clearly, the surface of the tablet is not predominately wax.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions specified in this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method of producing granules, which method comprises roll compaction of a 1,3-dihalo-5,5-dimethylhydantoin/binder blend, followed by feeding the compacted product obtained from the roll compactor into a mechanical device, where the compacted product is broken into granules; wherein said blend comprises
   (i) at least one powdery or finely-divided 1,3-dihalo-5,5-dialkylhydantoin in which each halogen atom is either chlorine or bromine, in which one of the alkyl groups in the 5-position is a methyl group, in which the other alkyl group in the 5-position has in the range of 1 to 4 carbon atoms, and in which the particle size is larger than about 20 microns, and
   (ii) a binder quantity of a micronized synthetic polyolefin-based hydrocarbon wax, wherein said binder quantity is in the range of about 0.5 to about 2 wt %, based on the total weight of said 1,3-dihalo-5,5-dialkylhydantoin and said wax;
   wherein said granules are produced at an increased granulation productivity in comparison to granules of the same 1,3-dihalo-5,5-dialkylhydantoin produced without a binder.

2. A method according to claim 1 wherein said other alkyl group of said 1,3-dihalo-5,5-dialkylhydantoin is a methyl group.

3. A method according to claim 1 wherein the 1,3-dihalo-5,5-dialkylhydantoin used in said pressure compacting has an average particle size of in the range of about 50 to about 600 microns.

4. A method according to claim 1 wherein the 1,3-dihalo-5,5-dialkylhydantoin used in said pressure compacting has an average particle size of in the range of about 175 to about 400 microns.

5. A method according to claim 1 wherein at least one halogen atom of said 1,3-dihalo-5,5-dialkylhydantoin is a bromine atom.

6. A method according to claim 5 wherein said 1,3-dihalo-5,5-dialkylhydantoin is 1,3-dibromo-5-isobutyl-5-methylhydantoin, 1,3-dibromo-5-n-propyl-5-methylhydantoin, 1,3-dibromo-5-ethyl-5-methylhydantoin, 1,3-bromochloro-5,5-dimethylhydantoin, 1,3-dibromo-5,5-dimethylhydantoin, or a mixture of two or more of the foregoing.

7. A method according to claim 1 wherein said wax has, prior to compaction, an average particle size of no greater than about 15 microns, a maximum particle size of no greater than about 40 microns, and a density in the range of about 0.9 to about 1.4 grams per cc at 25° C.

8. A method according to claim 1 wherein said wax is a polyethylene wax which, prior to compaction, melts at a temperature in the range of about 109° C. to about 111° C., has an average particle size in the range of about 6.0 to about 8.0 microns, and has a maximum particle size of about 22 microns.

9. A method according to claim 1 wherein said wax is a polypropylene wax having, prior to compaction, an average particle size in the range of about 5.0 to about 7.0 microns, a maximum particle size of about 22 microns, and a density in the range of about 0.9 to about 1.4 grams per cc at 25° C.

10. A method according to claim 1 wherein at least one halogen atom of said 1,3-dihalo-5,5-dialkylhydantoin is a bromine atom, and wherein said wax has, prior to compaction, an average particle size of no greater than about 15 microns, a maximum particle size of no greater than about 40 microns, and a density in the range of about 0.9 to about 1.4 grams per cc at 25° C.

11. A method according to claim 10 wherein the 1,3-dihalo-5,5-dialkylhydantoin used in said pressure compacting has an average particle size of in the range of about 50 to about 600 microns.

12. A method according to claim 10 wherein the 1,3-dihalo-5,5-dialkylhydantoin used in said pressure compacting has an average particle size of in the range of about 175 to about 400 microns.

13. A method according to claim 1 wherein said 1,3-dihalo-5,5-dialkylhydantoin is 1,3-dibromo-5-isobutyl-5-methylhydantoin, 1,3-dibromo-5-n-propyl-5-methylhydantoin, 1,3-dibromo-5-ethyl-5-methylhydantoin, 1,3-bromochloro-5,5-dimethylhydantoin, 1,3-dibromo-5,5-dimethylhydantoin, or a mixture of two or more of the foregoing; and wherein said wax has, prior to compaction, an average particle size of no greater than about 15 microns, a maximum particle size of no greater than about 40 microns, and a density in the range of about 0.9 to about 1.4 grams per cc at 25° C.

14. A method according to claim 1 wherein at least one halogen atom of said 1,3-dihalo-5,5-dialkylhydantoin is a bromine atom; and wherein said wax is a polyethylene wax which, prior to compaction, melts at a temperature in the range of about 109° C. to about 111° C., has an average particle size in the range of about 6.0 to about 8.0 microns, and has a maximum particle size of about 22 microns.

15. A method according to claim 14 wherein the 1,3-dihalo-5,5-dialkylhydantoin used in said pressure compacting has an average particle size of in the range of about 50 to about 600 microns.

16. A method according to claim 14 wherein the 1,3-dihalo-5,5-dialkylhydantoin used in said pressure compacting has an average particle size of in the range of about 175 to about 400 microns.

17. A method according to claim 1 wherein said 1,3-dihalo-5,5-dialkylhydantoin is 1,3-dibromo-5-isobutyl-5-methylhydantoin, 1,3-dibromo-5-n-propyl-5-methylhydantoin, 1,3-dibromo-5-ethyl-5-methylhydantoin, 1,3-bromochloro-5,5-dimethylhydantoin, 1,3-dibromo-5,5-dimethylhydantoin, or a mixture of two or more of the foregoing; and wherein said wax is a polyethylene wax which, prior to compaction, melts at a temperature in the range of about 109° C. to about 111° C., has an average particle size in the range of about 6.0 to about 8.0 microns, and has a maximum particle size of about 22 microns.

18. A method according to claim 1 wherein at least one halogen atom of said 1,3-dihalo-5,5-dialkylhydantoin is a bromine atom; and wherein said wax is a polypropylene wax having, prior to compaction, an average particle size in the range of about 5.0 to about 7.0 microns, a maximum particle size of about 22 microns, and a density in the range of about 0.9 to about 1.4 grams per cc at 25° C.

19. A method according to claim 18 wherein the 1,3-dihalo-5,5-dialkylhydantoin used in said pressure compacting has an average particle size of in the range of about 50 to about 600 microns.

20. A method according to claim 18 wherein the 1,3-dihalo-5,5-dialkylhydantoin used in said pressure compacting has an average particle size of in the range of about 175 to about 400 microns.

21. A method according to claim 1 wherein said 1,3-dihalo-5,5-dialkylhydantoin is 1,3-dibromo-5-isobutyl-5-methylhydantoin, 1,3-dibromo-5-n-propyl-5-methylhydantoin, 1,3-dibromo-5-ethyl-5-methylhydantoin, 1,3-bromochloro-5,5-dimethylhydantoin, 1,3-dibromo-5,5-dimethylhydantoin, or a mixture of two or more of the foregoing; and wherein said wax is a polypropylene wax having, prior to compaction, an average particle size in the range of about 5.0 to about 7.0 microns, a maximum particle size of about 22 microns, and a density in the range of about 0.9 to about 1.4 grams per cc at 25° C.

22. A method according to claim 1 wherein said binder quantity is in the range of about 0.5 to about 1 wt %, based on the total weight of said 1,3-dihalo-5,5-dialkylhydantoin and said wax.

23. A method according to claim 1 wherein said binder quantity is in the range of about 0.5 to about 1 wt %, based on the total weight of said 1,3-dihalo-5,5-dialkylhydantoin and said wax, and wherein the 1,3-dihalo-5,5-dialkylhydantoin used in said pressure compacting has an average particle size of in the range of about 50 to about 600 microns.

24. A method according to claim 1 wherein said binder quantity is in the range of about 0.5 to about 1 wt %, based on the total weight of said 1,3-dihalo-5,5-dialkylhydantoin and said wax, and wherein the 1,3-dihalo-5,5-dialkylhydantoin used in said pressure compacting has an average particle size of in the range of about 175 to about 400 microns.

25. A method according to claim 1 wherein said binder quantity is in the range of about 0.5 to about 1 wt %, based on the total weight of said 1,3-dihalo-5,5-dialkylhydantoin and said wax, and wherein at least one halogen atom of said 1,3-dihalo-5,5-dialkylhydantoin is a bromine atom.

26. A method according to claim 25 wherein said 1,3-dihalo-5,5-dialkylhydantoin is 1,3-dibromo-5-isobutyl-5-methylhydantoin, 1,3-dibromo-5-n-propyl-5-methylhydantoin, 1,3-dibromo-5-ethyl-5-methylhydantoin, 1,3-bromochloro-5,5-dimethylhydantoin, 1,3-dibromo-5,5-dimethylhydantoin, or a mixture of two or more of the foregoing.

27. A method according to claim 1 wherein said binder quantity is in the range of about 0.5 to about 1 wt %, based on the total weight of said 1,3-dihalo-5,5-dialkylhydantoin and said wax, and wherein said wax has, prior to compaction, an average particle size of no greater than about 15 microns, a maximum particle size of no greater than about 40 microns, and a density in the range of about 0.9 to about 1.4 grams per cc at 25° C.

28. A method according to claim 1 wherein said binder quantity is in the range of about 0.5 to about 1 wt %, based on the total weight of said 1,3-dihalo-5,5-dialkylhydantoin and said wax, and wherein said wax is a polyethylene wax which, prior to compaction, melts at a temperature in the range of about 109° C. to about 111° C., has an average particle size in the range of about 6.0 to about 8.0 microns, and has a maximum particle size of about 22 microns.

29. A method according to claim 1 wherein said binder quantity is in the range of about 0.5 to about 1 wt %, based on the total weight of said 1,3-dihalo-5,5-dialkylhydantoin and said wax, and wherein said wax is a polypropylene wax having, prior to compaction, an average particle size in the range of about 5.0 to about 7.0 microns, a maximum particle size of about 22 microns, and a density in the range of about 0.9 to about 1.4 grams per cc at 25° C.

30. A method according to claim 1 wherein said binder quantity is in the range of about 0.5 to about 1 wt %, based on the total weight of said 1,3-dihalo-5,5-dialkylhydantoin and said wax; wherein at least one halogen atom of said 1,3-dihalo-5,5-dialkylhydantoin is a bromine atom; and wherein said wax has, prior to compaction, an average particle size of no greater than about 15 microns, a maximum particle size of no greater than about 40 microns, and a density in the range of about 0.9 to about 1.4 grams per cc at 25° C.

31. A method according to claim 1 wherein said binder quantity is in the range of about 0.5 to about 1 wt %, based on the total weight of said 1,3-dihalo-5,5-dialkylhydantoin and said wax; wherein said 1,3-dihalo-5,5-dialkylhydantoin is 1,3-dibromo-5-isobutyl-5-methylhydantoin, 1,3-dibromo-5-n-propyl-5-methylhydantoin, 1,3-dibromo-5-ethyl-5-methylhydantoin, 1,3-bromochloro-5,5-dimethylhydantoin, 1,3-dibromo-5,5-dimethylhydantoin, or a mixture of two or more of the foregoing; and wherein said wax has, prior to compaction, an average particle size of no greater than about 15 microns, a maximum particle size of no greater than about 40 microns, and a density in the range of about 0.9 to about 1.4 grams per cc at 25° C.

32. A method according to claim 1 wherein said binder quantity is in the range of about 0.5 to about 1 wt %, based on the total weight of said 1,3-dihalo-5,5-dialkylhydantoin and said wax; wherein at least one halogen atom of said 1,3-dihalo-5,5-dialkylhydantoin is a bromine atom; and wherein said wax is a polyethylene wax which, prior to compaction, melts at a temperature in the range of about 109° C. to about 111° C., has an average particle size in the range of about 6.0 to about 8.0 microns, and has a maximum particle size of about 22 microns.

33. A method according to claim 32 wherein the 1,3-dihalo-5,5-dialkylhydantoin used in said pressure compacting has an average particle size of in the range of about 50 to about 600 microns.

34. A method according to claim 32 wherein the 1,3-dihalo-5,5-dialkylhydantoin used in said pressure compacting has an average particle size of in the range of about 175 to about 400 microns.

35. A method according to claim 1 wherein said binder quantity is in the range of about 0.5 to about 1 wt %, based on the total weight of said 1,3-dihalo-5,5-dialkylhydantoin and said wax; wherein at least one halogen atom of said 1,3-dihalo-5,5-dialkylhydantoin is a bromine atom; and wherein said wax is a polypropylene wax having, prior to compaction, an average particle size in the range of about 5.0 to about 7.0 microns, a maximum particle size of about 22 microns, and a density in the range of about 0.9 to about 1.4 grams per cc at 25° C.

36. A method according to claim 35 wherein the 1,3-dihalo-5,5-dialkylhydantoin used in said pressure compacting has an average particle size of in the range of about 50 to about 600 microns.

37. A method according to claim 35 wherein the 1,3-dihalo-5,5-dialkylhydantoin used in said pressure compacting has an average particle size of in the range of about 175 to about 400 microns.

38. A method according to claim 1 wherein said pressure compacting is conducted at a pressure in the range of about 500 to about 3,000 psi.

39. A method according to claim 1 wherein said pressure compacting is conducted at a pressure in the range of about 800 to about 1,500 psi.

* * * * *

UNITED STATES PATENT AND TRADEMARK OFFICE
CERTIFICATE OF CORRECTION

PATENT NO. : 6,965,035 B1
APPLICATION NO. : 10/202954
DATED : November 15, 2005
INVENTOR(S) : Jonathan N. Howarth et al.

It is certified that error appears in the above-identified patent and that said Letters Patent is hereby corrected as shown below:

Title page, Item (73) Assignee should read
--Assignee: Albemarle Corporation, Richmond, VA (US)--

Signed and Sealed this

Nineteenth Day of May, 2009

JOHN DOLL
*Acting Director of the United States Patent and Trademark Office*